United States Patent [19]
Pattee

[11] Patent Number: 6,142,667
[45] Date of Patent: Nov. 7, 2000

[54] GAS-SPRING ASSISTED, COUNTER-BALANCED L-ARM ASSEMBLY FOR FLUOROSCOPIC IMAGING

[75] Inventor: Jeff Pattee, Salt Lake City, Utah

[73] Assignee: OEC Medical Systems, Inc., Salt Lake City, Utah

[21] Appl. No.: 09/158,355

[22] Filed: Sep. 21, 1998

[51] Int. Cl.[7] .................................................. H05G 1/02
[52] U.S. Cl. .............................................. 378/198; 378/197
[58] Field of Search ............................ 378/37, 167, 177, 378/179, 193, 189, 195, 196, 197, 198, 204

[56] References Cited

U.S. PATENT DOCUMENTS

| | | |
|---|---|---|
| Re. 34,943 | 5/1995 | Van Endschot et al. . |
| 3,281,598 | 10/1966 | Hollstein . |
| 4,209,706 | 6/1980 | Nunan . |
| 4,447,721 | 5/1984 | Wang . |
| 4,716,581 | 12/1987 | Barud . |
| 4,768,216 | 8/1988 | Harvey et al. . |
| 4,797,907 | 1/1989 | Anderton . |
| 4,955,046 | 9/1990 | Siczek et al. ............................ 378/197 |
| 4,961,214 | 10/1990 | Van Endschot et al. . |
| 4,964,150 | 10/1990 | Van Der AA et al. .................. 378/197 |
| 5,014,293 | 5/1991 | Boyd et al. . |
| 5,050,197 | 9/1991 | Virta et al. ................................. 378/37 |
| 5,050,204 | 9/1991 | Siczek et al. . |
| 5,226,069 | 7/1993 | Narita . |
| 5,283,808 | 2/1994 | Cramer et al. . |
| 5,388,141 | 2/1995 | Hove ....................................... 378/197 |
| 5,426,683 | 6/1995 | O'Farrell, Jr. et al. . |
| 5,475,730 | 12/1995 | Galando . |
| 5,506,882 | 4/1996 | O'Farrell, Jr. et al. . |
| 5,544,217 | 8/1996 | Kadowaki et al. ...................... 378/198 |
| 5,583,909 | 12/1996 | Hanover . |
| 5,617,462 | 4/1997 | Spratt . |
| 5,627,873 | 5/1997 | Hanover et al. . |
| 5,642,395 | 6/1997 | Anderton et al. . |

OTHER PUBLICATIONS

International ISS Surgical Systems, Inc., ISS–2000 Plus Multispecialty Surgical Imaging System Brochure, pp. 1–25, 1991, Phoenix, Arizona.

*Primary Examiner*—David P. Porta
*Attorney, Agent, or Firm*—Thorpe, North & Western, LLP

[57] ABSTRACT

An X-ray positioning apparatus for a C-arm device that is "out of balance" in that a center of mass of the rotatable structure resides below an axis of lateral rotation of the C-arm. The positioning apparatus includes a conventional L-arm support for holding the C-arm thereon, wherein a torsional resistance device is disposed inside the L-arm. The torsional resistance device may be a gas spring, for example, pivotally attached at one end to a fixed location on a ground support such as a conventional base unit, and attached at an opposing end to the L-arm by a ball joint. The pivotal attachment of the gas spring resides below the axis of lateral rotation to thereby cause the gas spring to produce a torsional force about the axis of lateral rotation that is opposite in direction to torsional loads produced by force of gravity when the center of mass of the rotatable structure and the axis of lateral rotation are not in vertical alignment.

46 Claims, 3 Drawing Sheets

GAS-SPRING ASSISTED, COUNTER-BALANCED L-ARM ASSEMBLY FOR FLUOROSCOPIC IMAGING

BACKGROUND OF THE INVENTION

1. The Field of the Invention

The present invention relates generally to X-ray imaging systems. More particularly, it concerns a mobile C-arm assembly having a torsionally counterbalanced lateral rotation mechanism.

2. The Background Art

It is often desirable to take X-rays of a patient from a number of different positions, preferably without the need for frequent repositioning of the patient. Mobile C-arm X-ray diagnostic equipment, shown in FIG. 1, has been developed to meet these needs and has become well known in the medical art of surgical and other interventional procedures. By utilizing the now well-known C-arm design, X-rays of a patient can be made from several different angles and positions without repositioning the patient. The C-arm support structure for the X-ray equipment does not unduly encumber the space immediately surrounding the patient, which enables a physician to treat or otherwise attend to the patient without the need to repeatedly remove and replace the X-ray equipment.

Figure 1:
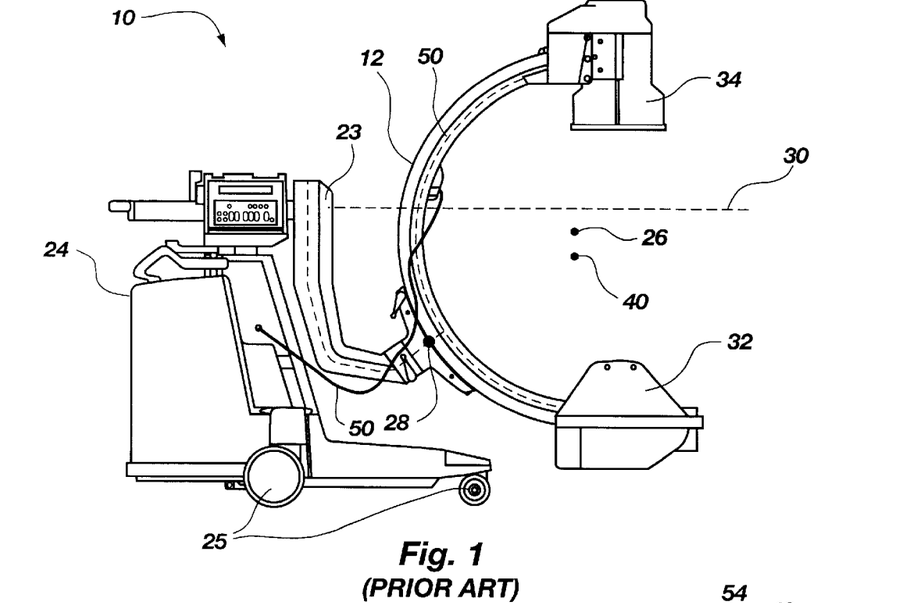
FIG. 1 is a side, elevational view of a C-arm apparatus exemplary of known prior art C-arm devices.

Referring to FIG. 1, there is shown a mobile C-arm apparatus exemplary of the prior art, the apparatus being designated generally at 10. The phrase "C-arm" refers generally to the elongate C-shaped member 12 terminating in opposing distal ends of the "C" shape shown in FIG. 1. An X-ray source 32 and an image receptor 34 are typically mounted at or near the distal ends, respectively, of the C-arm 12 in opposing orientation, with the C-arm 12 supported by an L-arm 23 in a suspended position. The space within the C-shape of the C-arm 12 provides room for a physician to attend to a patient substantially free of interference from the X-ray support structure. The support structure usually rests upon wheels 25 to enable the entire apparatus 10 to be wheeled from room to room, and along the length of a patient while the physician operates or examines, ensuring that devices such as cardiac catheters, long bone nails, etc. are properly positioned during the procedure.

The C-arm 12 is usually mounted so as to enable rotational movement of the arm in two degrees of freedom, i.e. about two perpendicular axes, namely, an axis of orbital rotation 26 and an axis of lateral rotation 30 that is coincident with the axis of rotation of L-arm 23. More specifically, the C-arm 12 is slidably mounted to the L-arm 23 to enable orbiting rotational movement of the C-arm 12 about the axis of orbital rotation 26, thereby permitting the X-ray source 32 and the image receptor 34 to be selectively oriented vertically, horizontally, or somewhere in between. The C-arm 12 is also laterally rotatable by rotational movement of the L-arm 23 about the axis of lateral rotation 30, i.e. in a perpendicular direction relative to the orbiting direction to enable selectively adjustable positioning of the X-ray source 32 and receptor 34 relative to both the width and length of the patient. The rotatable movability of the C-arm 12 about both axes 26 and 30 allows the physician to take X-rays of the patient at an optimal angle as determined with respect to the particular anatomical condition being imaged.

Designers and manufacturers of C-arm equipment are faced with a number of challenges. The support structure used to support and rotate a C-arm in its various suspended positions must be strong enough to withstand tremendous torsional, tensile and compressive stresses. The support structure must also be heavy enough and have a large enough footprint to avoid tipping over upon lateral rotation of the C-arm 12 and L-arm 23 about the axis of lateral rotation 30, which causes the center of mass of the equipment to shift dramatically.

It is also desirable to balance the rotatable structure (i.e. the C-arm 12, X-ray source 32, image receptor 34, and L-arm 23) such that relatively little physical effort is required to move the C-arm 12 about the axes 26 and 30. One way of accomplishing this is to design the rotatable structure such that its center of mass resides as closely as possible, if not coincident with, the axes 26 and 30, in which case very little torsional force is required to move the C-arm about the axes 26 and 30, and thus very little physical effort is required.

However, in some C-arm designs the center of mass of the rotatable structure necessarily resides spaced apart from the axis of lateral rotation 30 by a substantial separation distance, to gain advantages in certain clinical applications. Such C-arm designs are referred to as being "unbalanced" about the axis of lateral rotation. In such unbalanced designs, significant torsional force must be applied when rotating the L-arm 23 about the axis of lateral rotation 30. Although the average physician generally has sufficient physical strength with which to physically rotate the L-arm about its axis of lateral rotation, the physical exertion required detracts from other, more important tasks to be carried out by the physician. Further, an unbalanced design can be dangerous to the patient and the operator. For example, a much sturdier and more powerful braking mechanism is required to prevent the C-arm 12 from falling violently downward, whereby it could strike and injure an unsuspecting person.

Some attempts have been made to reduce the amount of physical exertion required to rotate and position the L-arm 23 about the axis of lateral rotation 30. Exemplary of such prior art attempts is U.S. Pat. No. 4,955,046 (issued to Siczek et al. on Sep. 4, 1990) which discloses a conventional C-arm apparatus having an L-arm. The device includes a gear-driven mechanism controlled by a hand crank for rotating the L-arm about its axis of lateral rotation. The physical exertion problem mentioned above is thus overcome by the hand crank gear mechanism, but the hand crank is tedious and time-consuming to use.

It is noteworthy that none of the prior art known to applicant provides a counterbalancing mechanism to overcome the "unbalanced" condition produced when the center of mass of the Rotatable structure is separated by a large distance from the axis of lateral rotation. There appears to be a long felt need in the field of C-arm X-ray imaging equipment for a counter-balancing mechanism for use in rotatable structure that is "unbalanced" about the axis of lateral rotation.

OBJECTS AND SUMMARY OF THE INVENTION

It is therefore an object of the present invention to provide an X-ray positioning apparatus having a torsionally counterbalanced lateral rotation mechanism.

It is another object of the present invention to provide such an X-ray positioning apparatus that is simple in design and manufacture.

The above objects and others not specifically recited are realized in a specific illustrative embodiment of an X-ray positioning apparatus for a C-arm device that is "out of balance" in that a center of mass of the rotatable structure resides below an axis of lateral rotation of the C-arm. The positioning apparatus includes a conventional L-arm support for holding the C-arm thereon, wherein a torsional resistance device is disposed inside the L-arm. The torsional resistance device may be a gas spring, for example, pivotally attached at one end to a fixed location on a ground support such as a conventional base unit, and attached at an opposing end to the L-arm by a ball joint. The pivotal attachment of the gas spring resides below the axis of lateral rotation to thereby cause the gas spring to produce a torsional force about the axis of lateral rotation that is opposite in direction to torsional loads produced by force of gravity when the center of mass of the rotatable structure and the axis of lateral rotation are not in vertical alignment.

Additional objects and advantages of the invention will be set forth in the description which follows, and in part will be apparent from the description, or may be learned by the practice of the invention without undue experimentation. The objects and advantages of the invention may be realized and obtained by means of the instruments and combinations particularly pointed out in the appended claims.

BRIEF DESCRIPTION OF THE DRAWINGS

The above and other objects, features and advantages of the invention will become apparent from a consideration of the subsequent detailed description presented in connection with the accompanying drawings in which.

DETAILED DESCRIPTION

For the purposes of promoting an understanding of the principles in accordance with the invention, reference will now be made to the embodiments illustrated in the drawings and specific language will be used to describe the same. It will nevertheless be understood that no limitation of the scope of the invention is thereby intended. Any alterations and further modifications of the inventive features illustrated herein, and any additional applications of the principles of the invention as illustrated herein, which would normally occur to one skilled in the relevant art and having possession of this disclosure, are to be considered within the scope of the invention claimed.

Applicant has discovered that the operability of an "unbalanced" C-arm apparatus, in particular one whose center of mass does not coincide with the axis of lateral rotation, is greatly enhanced by the addition of a torsionally counterbalanced lateral rotation mechanism. Applicant has added a device that reduces and in some cases almost eliminates the effect of gravity-induced torsion in the movement of the C-arm apparatus about its axis of lateral rotation.

It will be appreciated that prior art C-arm devices, exemplified in FIG. 1, often include a downwardly-extending L-arm 23 slidably attached to a C-arm 12 at attachment point 28. The L-arm 23 is held in suspension by a support base 24, and a high voltage cable 50 extends from the support base 24 through the L-arm 23 and C-arm 12 into connection with the X-ray source 32 and image receptor 34 to supply adequate power thereto. The C-arm 12 is orbitable about axis of orbital rotation 26, while the L-arm 23 is rotatable about axis of lateral rotation 30 to thereby rotate the C-arm 12 laterally. An image receptor 34 and an X-ray source 32, in combination with the L-arm 23 and C-arm 12, comprise collectively an X-ray assembly having a center of mass 40 residing below axis of lateral rotation 30. This configuration produces an eccentric, lateral moment arm under force of gravity when the L-arm 23 is rotated about the axis of lateral rotation 30, and therefore requires effort of the physician.

Figures 2, 3:
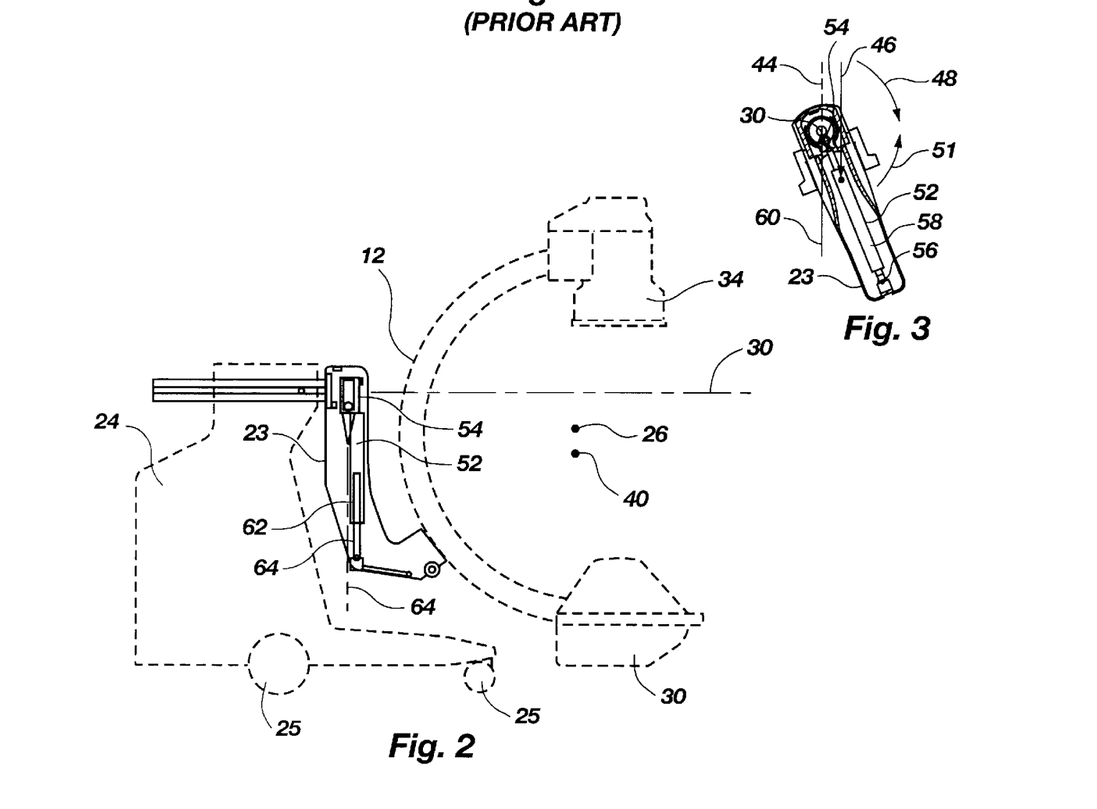
FIG. 2 is a side, elevational view of a C-arm positioning device, made in accordance with the principles of the present invention.
FIG. 3 is a front, rotated, partial cross-sectional view of the C-arm positioning device of FIG. 2.

Referring now to FIGS. 2–3, it will be appreciated by those of ordinary skill in the fields of physics and engineering that gravity does not produce torsional force about the axis of lateral rotation 30 when the X-ray system's center of mass 40 resides in vertical alignment with the axis 30. However, as also understood by those in the fields of physics and engineering, once the L-arm 23 is rotated to any extent about the axis of lateral rotation 30 to move the center of mass 40 out of vertical alignment with the axis 30, an eccentricity arises whereby gravitational force 46 acts upon a moment arm (the perpendicular distance between the center of mass 40 and a vertical line 44 passing through the axis of lateral rotation 30) and produces a torsional load 48 about the axis 30. This torsional load 48 could be described as tending to "tip" the X-ray equipment over unless counteracted by the weight of the equipment, and/or by a counteracting force. The torsional load 48 impedes efforts to rotate the L-arm 23 about the axis of lateral rotation 30, making it more difficult for physicians to rotate the L-arm 23.

Applicant has invented a device to provide a counteracting torsional load 51 opposite in direction to the torsional load 48 produced under the force 46 of gravity, in the form of a strategically placed gas spring 52. The gas spring 52 preferably resides inside the L-arm 23 as shown. Although the invention relates to a counter-balance of all of the suspended components of the C-arm device, the C-arm 12, X-ray source 30 and image receptor 34 are simply depicted in phantom line in FIG. 2 because the key workings of the present invention relate to the L-arm 23. The support base 24 is also depicted in phantom line in FIG. 2.

By attaching one end of a gas spring 52 to a pivotal ground point 54 (explained in more detail below), and the other end to a point 56 on the L-arm 23, the gas spring 52 produces a counteracting force 58 against the L-arm 23. As shown in FIG. 3, when the L-arm 23 is in any rotated position (any position other than vertical alignment with the axis of lateral rotation 30), the force 58 from the gas spring 52 operates along the axis of the gas spring 52, producing vertical and horizontal components of the force 58. The horizontal component of the force 58 helps produce the counteracting torsional load 51. As such, the gas spring 52 can be designed to reduce the effects of the gravitational torsion 48, and even eliminate the torsion 48 for some rotated positions of the L-arm 23.

The force 58 from the gas spring 52 pivots about the ground point 54 as the L-arm 23 rotates. When the L-arm 23 is rotated to an offset position as in FIG. 3, the external forces involved can be summarized as follows:

Vertical Direction. Gravitational force 46 acts downwardly against the X-ray equipment, and a component of the force 58 from the gas spring 52 acts vertically downwardly against the L-arm 23, both of which are counteracted by the base support 24 acting upwardly on the L-arm 23 at the axis of lateral rotation 30 by upward force 60.

Torsional Direction. A portion of gravitational force 46 is offset from the axis of lateral rotation 30 when the center of mass 40 is offset from the axis 30, producing a "clockwise" directed torsional force 48, which is counteracted by the force 58 produced by the gas spring 52 which produces a "counter-clockwise" directed torsional force 51 because the ground point 54 of attachment of the gas spring 52 is offset from the axis of lateral rotation 30.

Briefly and summarily stated, the placement of a source of compression force 58 such as the gas spring 52 which acts against the L-arm 23 from a ground point that does not coincide with the axis of lateral rotation 30 (in this case ground point 54), can be used to produce the counteracting torsional load 51. The magnitude of the force 58 can be designed as known by those of ordinary skill in the relevant physics and engineering to produce the counteracting torsion 51 to have a magnitude that substantially matches the magnitude of the gravitational torsion 48. of course, the magnitudes of the gravitational torsion 48 and the counteracting torsion 51 change as the L-arm 23 pivots about the axis of lateral rotation 30, as will be appreciated to those having ordinary skill in the relevant physics and engineering. Therefore, if the force 58 is relatively constant, the change in the magnitude of the counteracting torsion 51 will also be relatively consistent with the change in gravitational torsion 48 at all positions of the L-arm 23. The majority effect of the gravitational torsion 48 will still be overcome by the counteracting torsion 51 produced by the gas spring 52 for all orientations of the L-arm 32.

The ground point 54 is preferably a pivotal attachment of the gas spring 52 to a brake drum (shown in FIG. 5) of the L-arm 23, the brake drum being attached to the base support 24 and therefore being taken as a ground point. The attachment point 56 is preferably a ball joint (shown most clearly in FIG. 5) as known in the field of mechanical joints, and is therefore a universal joint for permitting three-dimensional motion.

In broad terms, the L-arm 23 and C-arm 12 may be described in combination as a suspension means movably coupled to the support base 24 at a first pivotal attachment point for holding an X-ray source 32 and an image receptor 34 in a suspended position and for rotating said X-ray source 32 and image receptor 34 relative to said support base 24 about a rotational movement path into various positions.

The gas spring 52 is only one example of a means for producing torsional force. Any suitable device or method for producing torsion is within the scope of the present invention, whether now known or later devised, because the invention includes the broad concept of simply producing torsion about the axis of lateral rotation 30 to counteract the effects of gravitational torsion produced when the center of mass of the rotatable structure does not coincide with said axis of lateral rotation 30. A torsion spring, a compression spring, an extension spring, or any suitable spring force device, or any other suitably placed source of torsional force may be utilized in lieu of the gas spring 52.

It will be appreciated that the gas spring 52 (or any equivalent thereof as explained above) may be described broadly herein as a reinforcing means for applying a supporting force to suspension means (such as the combination L-arm 23 and C-arm 12) in addition to any supporting force provided by the support base 24. The concept of "supporting force provided by the support base 24" includes any pivot connection between the support base 24 and L-arm 23, including any nuts, bolts or other fastening devices, in short any feature of the support base that operates to hold the L-arm 23 in place is included in the concept of "supporting force." Therefore, any further force besides the a "supporting force" as described above falls within the scope of the "reinforcing means," the gas spring 52 being simply one version thereof.

The gas spring 52 (or any equivalent thereof as explained above) may also be described broadly herein as a compression means coupled to the support base 24 for providing added support to the suspension means (such as the combination L-arm 23 and C-arm 12). It will be appreciated that the gas spring 52 may be alternately described as providing support to the suspension means (L-arm 23 and C-arm 12), or to the X-ray assembly (L-arm 23, C-arm 12, X-ray source 32 and image receptor 34).

Figure 4A:
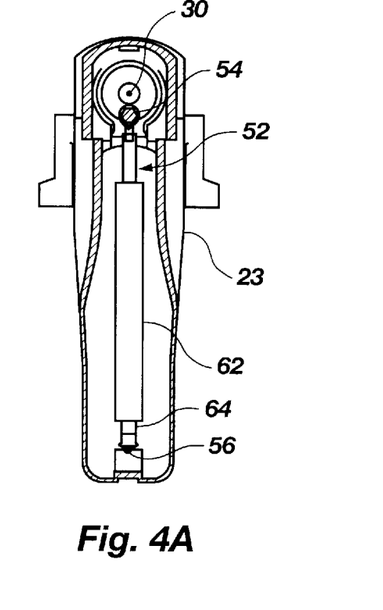
FIG. 4A is a front, cross-sectional view of the C-arm positioning device of FIG. 2, shown in a first, unrotated or "neutral 0°" position.
Figure 4B:
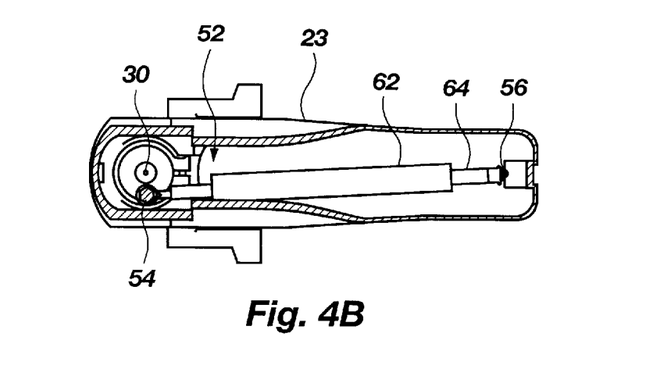
FIG. 4B is a front, cross-sectional view of the C-arm positioning device of FIG. 2, shown in a "+90°" rotated position.
Figure 4C:
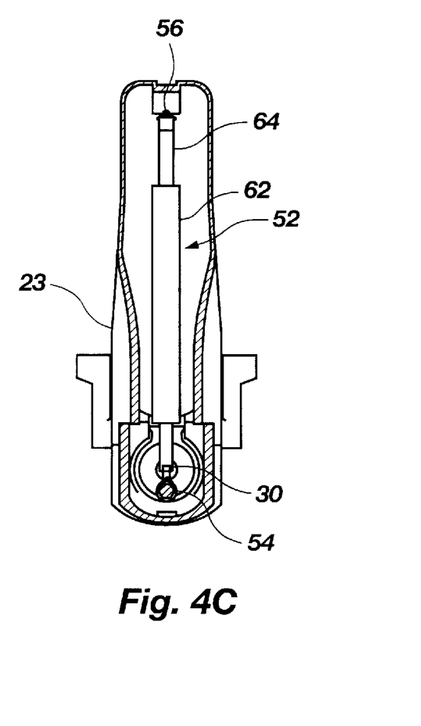
FIG. 4C is a front, cross-sectional view of the C-arm positioning device of FIG. 2, shown in a "180°" rotated position.

Stated another way, the gas spring 52 may also be described as an expansion/contraction means pivotally connected to the support base 24 and to the suspension means (i.e. L-arm 23) for applying a compression force 58 to said suspension means in a direction that does not intercept the axis of lateral rotation 30, a condition which exists when the L-arm 23 is in a rotated position other than 0° or 180° (as shown in FIGS. 4A and 4C, respectively).

As shown in FIGS. 4A–4D, the gas spring 52 resides in a retracted condition when disposed in the 0° unrotated position of FIG. 4A. As the L-arm rotates, the pivotal ground point 54 remains fixed, thereby causing the gas spring 52 to expand responsive to upward pivotal movement of the L-arm 23 (note the upward-most position at the 180° position shown in FIG. 4C shows the gas spring 52 in its most expanded condition), and to contact responsive to downward pivotal movement of the L-arm.

The gas spring 52 (or any equivalent thereof as explained above) may also be described broadly herein as a counterbalancing means for applying torsional resistance to the suspension means (L-arm 23 and C-arm 12) to thereby resist opposing torsional loads produced about the axis of lateral rotation 30.

It is often the case that the center of mass 40 resides at least three inches below the axis of lateral rotation 30, for example, by four inches. In such a case, given the weight of the various X-ray equipment components (L-arm 23, C-arm 12, X-ray source 32, image receptor 34), it is preferred to utilized a gas spring 52 that produces about 900–920 pounds of compression force, with the pivotal ground point 54 residing preferably about 1.2 inches below the axis of lateral rotation 30, and thus within 1–2 inches between said axis 30. As such, the pivotal ground point 54 preferably resides below the axis of lateral rotation 30 and above the center of mass 40.

Another aspect of the invention, as depicted in FIGS. 2–3, is described as follows. A line extending between the pivotal ground point 54 and the attachment joint 56 is nonhorizontal and nonvertical (note comparison with vertical line 64 in FIG. 2) when the X-ray positioning apparatus (equipment components L-arm 23, C-arm 12, X-ray source 32, image receptor 34) is disposed in a normal, operative working position, such that rotational movement of the L-arm 23 about the axis of lateral rotation 30 produces pivotal movement at the attachment joint 56 in multiple planes, and wherein the attachment joint comprises a universal joint.

It will be appreciated that the main portion of the L-arm 23 extends in a generally nonstraight path, and that the gas spring 52 extends in a generally straight path. It will also be seen by inspection of FIGS. 4A–4D that the orientation of the gas spring 52 with respect to the L-arm changes with rotational movement of the L-arm about the axis of lateral rotation 30. The gas spring 52 is thus preferably in a nonparallel orientation with respect to the main portion of the L-arm 23, in most if not all positions of the L-arm 23.

The gas spring 52 is preferably configured, designed and positioned to produce the counteracting torsional force 51 to have a magnitude of at least 500 inch-pounds about the axis of lateral rotation 30, more preferably at least 800 inch-pounds, and most preferably at least 1,000 inch-pounds.

Figure 4D:
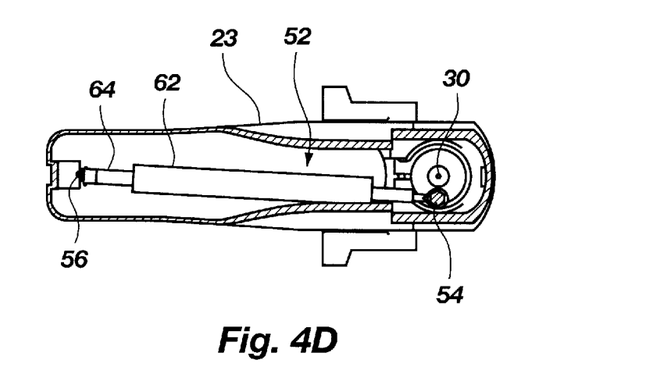
FIG. 4D is a front, cross-sectional view of the C-arm positioning device of FIG. 2, shown in a "270°" or "−90°" rotated position.

Referring now to FIGS. 4A–4D, there is shown the L-arm 23 and the attached gas spring 52 in various positions of rotation. In FIG. 4A, the L-arm 23 is shown disposed in a first, unrotated or "neutral 0°" position. In FIG. 4B, the L-arm 23 is shown disposed in a "+90°" rotated position. In FIG. 4C, the L-arm 23 is shown disposed in a "180°" rotated position. In FIG. 4D, the L-arm 23 is shown disposed in a "270°" or "−90°" rotated position.

It will be appreciated that the gas spring 52 includes a cylinder body 62 and a shaft 64 slidably disposed within said cylinder body 62. The gas spring 52 operates as known in the art to produce a compression force, preferably approximately 900–920 pounds, with some small variation in the force depending on how far the shaft 64 extends from the cylinder body 62. As such, the gas spring 52 can be designed to produce a desired magnitude of compression force which, in combination with the distance between ground point 54 and the axis of lateral rotation 30, operates to produce a counteracting torsional force 51 that is equivalent to the gravitational torsional force 48 for at least one position of the L-arm 23.

Since the ground point 54 remains fixed, the gas spring 52 necessarily increases in length as the L-arm 23 is rotated upwardly about the axis of lateral rotation 30. Conversely, the gas spring 52 decreases in length as the L-arm 23 is rotated downwardly, by retraction of the shaft 64 back into the cylinder body 62.

Figure 5:
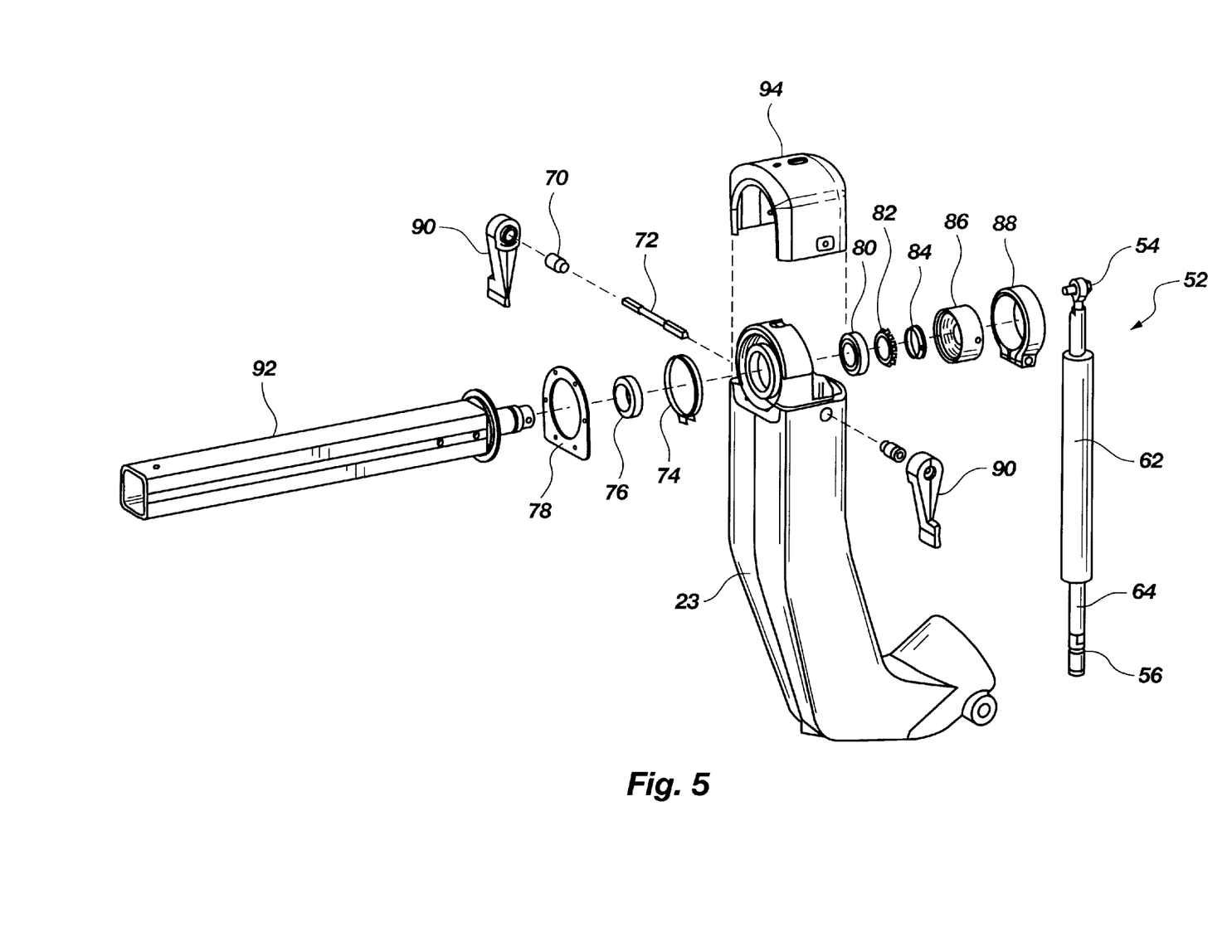
FIG. 5 is an exploded, perspective view of the C-arm positioning device of FIG. 2.

In FIG. 5 there is shown an exploded, perspective view of the L-arm 23 and the gas spring 52 with various operative components of the interface between the L-arm 23 and the base support 24. It will be appreciated that the L-arm 23 includes a braking mechanism to hold it in place in a desired rotational orientation, including the components of a brake actuator 70, brake shaft 72, rotation stop 74, bearing 76, cover plate 78, bearing 80, lock washer 82, lock nut 84, brake drum 86, brake shoe 88, and a pair of handles 90 for selectively actuating and releasing the braking components from application to the L-arm 23. An L-arm cap 94 attaches to the L-arm 23 and covers the components.

A cross arm 92 is a component of the support base 24 and supports the L-arm 23 thereon, and the brake drum 86 is preferably fixedly attached to the cross arm 92. The gas spring 52 is preferably pivotally attached to the brake drum 86 at 54 (FIGS. 2 and 3), and point 54 is therefore a ground point, because the brake drum 86 is essentially a fixed extension of the base support 24 which resides upon the ground in a stationary position during operation. Of course, the base support 24 is preferably mobile by its wheels 25 for moving from one location to another, typically between rooms in a health care facility.

In accordance with the features and combinations described above, a preferred method of positioning an X-ray apparatus includes the steps of:

(a) suspending an X-ray source and an image receptor with support from a suspension means that is rotatable about an axis of lateral rotation, wherein the X-ray source and the image receptor and the suspension means collectively comprise an X-ray assembly having a center of mass residing in a non-coaxial orientation with respect to said axis of lateral rotation;

(b) rotating the suspension means about the axis of lateral rotation to thereby produce a gravitational torsional force about said axis of lateral rotation; and (c) coupling a torsion-producing means to the suspension means to thereby produce counteracting torsion about the axis of lateral rotation that is opposite in direction to the gravitational torsional force.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements. Thus, while the present invention has been shown in the drawings and fully described above with particularity and detail in connection with what is presently deemed to be the most practical and preferred embodiment(s) of the invention, it will be apparent to those of ordinary skill in the art that numerous modifications, including, but not limited to, variations in size, materials, shape, form, function and manner of operation, assembly and use may be made without departing from the principles and concepts set forth herein.

What is claimed is:

1. An X-ray positioning apparatus comprising:
   a support base;
   a C-arm, and an X-ray source and an image receptor mounted upon opposing locations, respectively, on the C-arm;
   a support arm pivotally attached at one end thereof to a first pivotal attachment point on the support base and slidably attached at a second end thereof to the C-arm, wherein the first pivotal attachment point coincides with an axis of lateral rotation such that the support arm is selectively rotatable relative to the support base about said axis of lateral rotation to selected lateral positions;
   a gas spring pivotally attached to a second pivotal attachment point on the support base and extending away from said second pivotal attachment point into a third attachment point on the support arm, wherein said second pivotal attachment point is spaced apart from the first pivotal attachment point, and wherein the entire gas spring resides inside the support arm.

2. The apparatus of claim 1, wherein the support arm, C-arm, X-ray source and image receptor collectively comprise an X-ray assembly having a center of mass, and wherein the second pivotal attachment point resides below the first pivotal attachment point to thereby enable the gas spring to apply a counteracting torsional force against an out-of-balance torsional force produced when the center of mass of the X-ray assembly resides out of vertical alignment with the axis of lateral rotation.

3. The apparatus of claim 1, wherein a majority portion of the support arm comprises an elongate member and wherein the gas spring comprises an elongate member, and wherein said gas spring is disposed in a nonparallel orientation with respect to said majority portion of the support arm for a majority of positions of said support arm relative to the support base to thereby produce a desired amount of torsional force about the axis of lateral rotation.

4. The apparatus of claim 1, wherein the C-arm and the X-ray source and the image receptor and the support arm collectively comprise an X-ray assembly having a center of mass that resides below the axis of lateral rotation when the support arm resides in a first, unrotated position.

5. The apparatus of claim 4, wherein the center of mass of the X-ray assembly resides at least three inches below the axis of lateral rotation when the support arm resides in the first, unrotated position.

6. The apparatus of claim 1, wherein a line extending between the second pivotal attachment point and the third attachment point is nonhorizontal and nonvertical for a for a majority of positions of the support arm relative to the support base when the X-ray positioning apparatus is disposed in a normal, operative working position, such that rotational movement of the support arm about the axis of lateral rotation produces pivotal movement at the third attachment point in multiple planes, and wherein the third attachment point comprises a universal joint.

7. The apparatus of claim 1, wherein the second pivotal attachment point resides below the first pivotal attachment point and above a center of mass of the X-ray system when the support arm resides in a first, unrotated position.

8. The apparatus of claim 7, wherein the second pivotal attachment point resides below the first pivotal attachment point by a distance within a range of approximately one inch to two inches, and wherein the center of mass of the X-ray system resides below the axis of lateral rotation by a distance of at least three inches.

9. The apparatus of claim 1, wherein the gas spring includes a means for applying a compression force to the support arm, said gas spring being connected to the support arm and to the support base in an arrangement which, in combination with the compression force, operates to produce a counteracting torsional force about the axis of lateral rotation substantially equivalent to an opposing torsional force produced about said axis of lateral rotation by force of gravity when the support arm is disposed in a displaced, rotated position.

10. The apparatus of claim 9, wherein the C-arm and the X-ray source and the image receptor and the support collectively comprise an X-ray assembly having a center of mass, and wherein said center of mass being spaced-apart from the axis of lateral rotation by a separation distance and is thereby disposed in an orbital movement path about said axis of lateral rotation by rotational movement of the support arm, and wherein a combination of the separation distance and amount of weight of the X-ray assembly requires the compression force applied by the gas spring to exceed nine hundred pounds in order to produce the counteracting torsional force that is substantially equivalent to the opposing torsional force produced by force of gravity.

11. The apparatus of claim 1, wherein the support arm comprises an elongate member having a central axis, and wherein the gas spring comprises an elongate member having a central axis that remains in a nonparallel orientation with respect to the central axis of the support arm.

12. A method of positioning an X-ray apparatus, said method comprising the steps of:

(a) suspending an X-ray source and an image receptor with support from a suspension means including a support arm that is rotatable about an axis of lateral rotation, wherein the X-ray source and the image receptor and the suspension means collectively comprise an X-ray assembly having a center of mass residing in a non-coaxial orientation with respect to said axis of lateral rotation;

(b) rotating the suspension means about the axis of lateral rotation to thereby produce a gravitational torsional force about said axis of lateral rotation; and (c) counteracting the torsional force using a torsion-producing means disposed on the support arm to thereby produce counteracting torsion about the axis of lateral rotation that is opposite in direction to the gravitational torsional force.

13. An X-ray positioning apparatus comprising:

a support base;

suspension means pivotally attached to the support base for holding an X-ray source and an image receptor in a suspended position and for rotating said X-ray source and image receptor relative to said support base about an axis of lateral rotation, the suspension means including a support arm pivotally attached to the support base; and counter-balancing means, disposed on the support arm and pivotal therewith, for applying torsional resistance to the suspension means to thereby resist opposing torsional loads produced about the lateral axis.

14. The apparatus of claim 13, wherein the counter-balancing means comprises means for producing a torsional resistance of at least 500 inch-pounds about the lateral axis.

15. The apparatus of claim 13, wherein the counter-balancing means comprises means for producing a torsional resistance of at least 800 inch-pounds about the lateral axis.

16. The apparatus of claim 13, wherein the counter-balancing means comprises means for producing a torsional resistance of at least 1,000 inch-pounds about the lateral axis.

17. The apparatus of claim 13, further comprising an X-ray assembly formed in part by the suspension means, said suspension means including a C-arm slidably attached to the support arm, said X-ray assembly further comprising an X-ray source and an image receptor, wherein the X-ray assembly has a center of mass that resides below the axis of lateral rotation when the support arm resides in a first, unrotated position.

18. The apparatus of claim 13, wherein the counter-balancing means comprises an expansion/contraction means pivotally connected to the support base and to the suspension means for applying a compression force to said suspension means in a direction that does not intercept the axis of lateral rotation.

19. The apparatus of claim 13, wherein the expansion/contraction means comprises a gas spring.

20. The apparatus of claim 13, wherein the counter-balancing means comprises an expansion/contraction means for expanding responsive to upward pivotal movement of at least a portion of the suspension means and contracting responsive to downward pivotal movement of said portion of the suspension means.

21. The apparatus of claim 13, wherein the suspension means comprises a C-arm slidably attached to the support arm, and wherein the entire counter-balancing means resides inside the support arm.

22. An X-ray positioning apparatus comprising:

a support base;

an X-ray assembly comprising an X-ray source, an image receptor, and a suspension means pivotally connected to the support base at an axis of lateral rotation for holding the X-ray source and the image receptor in suspended positions and for rotating said X-ray source and image receptor about the axis of lateral rotation, the suspension means including a support arm pivotally attached to the support base; and compression means, disposed on the support arm and coupled to the support base, for providing added support to the X-ray assembly by applying a compression force to said X-ray assembly.

23. The apparatus of claim 22, wherein the compression means is positioned in a manner and arrangement that causes the compression force to produce torsion about the axis of lateral rotation.

24. The apparatus of claim 22, wherein a majority portion of the suspension means comprises an elongate member and wherein the compression means comprises an elongate member, and wherein said compression means remains disposed in a nonparallel orientation with respect to said majority portion of the suspension means for a majority of positions of said suspension means relative to the support base to thereby produce a desired amount of torsional force about the axis of lateral rotation.

25. The apparatus of claim 22, wherein the X-ray assembly has a center of mass that resides below the axis of lateral rotation when the suspension means resides in a first, unrotated position.

26. The apparatus of claim 25, wherein the center of mass of the X-ray assembly resides at least three inches below the axis of lateral rotation when the suspension means resides in the first, unrotated position.

27. The apparatus of claim 22, wherein the support arm is pivotally attached at one end thereof to a first pivotal attachment point on the support base coinciding with the axis of lateral rotation, and wherein the compression means is pivotally attached to a second pivotal attachment point on the support base and extends away from said second pivotal attachment point into a third attachment point on the support arm, wherein said second pivotal attachment point is spaced apart from the first pivotal attachment point.

28. The apparatus of claim 27, wherein a line extending between the second pivotal attachment point and the third attachment point is nonhorizontal and nonvertical when the X-ray positioning apparatus is disposed in a normal, operative working position, such that rotational movement of the suspension means about the axis of lateral rotation produces pivotal movement at the third attachment point in multiple planes, and wherein the third attachment point comprises a universal joint.

29. The apparatus of claim 27, wherein the second pivotal attachment point resides below the first pivotal attachment point and above a center of mass of the X-ray system when the suspension means resides in a first, unrotated position.

30. The apparatus of claim 29, wherein the second pivotal attachment point resides below the first pivotal attachment point by a distance within a range of approximately one inch to two inches, and wherein the center of mass of the X-ray system resides below the axis of lateral rotation by a distance of at least three inches.

31. The apparatus of claim 27, wherein the compression means is connected to the suspension means and to the support base in an arrangement which, in combination with the compression force, operates to produce a counteracting torsional force about the axis of lateral rotation substantially equivalent to an opposing torsional force produced about said axis of lateral rotation by force of gravity when the suspension means is disposed in a displaced, rotated position.

32. The apparatus of claim 31, wherein a center of mass of the X-ray assembly is spaced-apart from the axis of lateral rotation by a separation distance and is thereby disposed in an orbital movement path about said axis of lateral rotation by rotational movement of the suspension means, and wherein a combination of the separation distance and amount of weight of the X-ray assembly requires the compression force applied by the compression means to exceed nine hundred pounds in order to produce the counteracting torsional force that is substantially equivalent to the torsional force produced by force of gravity.

33. The apparatus of claim 22, wherein the compression means comprises a gas spring.

34. The apparatus of claim 22, wherein the suspension means comprises an elongate member having a central axis, and wherein the compression means comprises an elongate member connected to the support base at a point of attachment and extending from said point of attachment into another point of attachment to the suspension means, said compression means having a central axis that remains in a nonparallel orientation with respect to the central axis of the suspension means.

35. The apparatus of claim 22, wherein the suspension means comprises a C-arm slidably attached to the support arm, and wherein the entire compression means resides inside the support arm.

36. An X-ray positioning apparatus for use with X-ray diagnostic equipment, said apparatus comprising:

a support base;

suspension means movably coupled to the support base at a first pivotal attachment point for holding an X-ray source and an image receptor in a suspended position and for rotating said X-ray source and image receptor relative to said support base about a rotational movement path into various positions, the suspension means including a support arm pivotally attached to the support base; and reinforcing means, disposed on the support arm and movable therewith, for applying a supporting force to the suspension means in addition to any supporting force provided by the support base.

37. The apparatus of claim 36, wherein the suspension means comprises a C-arm slidably attached to the support arm, and wherein the entire reinforcing means resides inside the support arm.

38. The apparatus of claim 36, wherein the suspension means and the X-ray source and the image receptor collectively comprise an X-ray assembly having a center of mass, and wherein the reinforcing means is coupled to the support base at a second attachment point residing below the first attachment point to thereby enable said reinforcing means to apply a counteracting torsional force against an out-of-balance torsional force produced when the center of mass of the X-ray assembly resides out of vertical alignment with the first pivotal attachment point.

39. The apparatus of claim 36, wherein the reinforcing means comprises a means for applying the supporting force to the suspension means in a different direction than any supporting forces provided by the support base.

40. The apparatus of claim 36, wherein the reinforcing means comprises an expansion/contraction means for expanding responsive to upward pivotal movement of at least a portion of the suspension means and contracting responsive to downward pivotal movement of said portion of the suspension means.

41. The apparatus of claim 40, wherein the expansion/contraction means is attached at a first portion thereof to a stationary location on the support base and at a second portion thereof to a portion of the suspension means that is movable with respect to the support base.

42. The apparatus of claim 40, wherein the expansion/contraction means further comprises a gas spring.

43. The apparatus of claim 42, wherein the reinforcing means comprises a C-arm slidably attached to the support arm, said support arm including a main, elongate portion and wherein the gas spring extends generally along a straight direction that is nonparallel with the main, elongate portion of the support arm.

44. The apparatus of claim 42, wherein the entire gas spring resides inside the support arm.

45. An X-ray positioning apparatus comprising:
  a support base;
  a C-arm, and an X-ray source and an image receptor mounted upon opposing locations, respectively, on the C-arm;
  a support arm pivotally attached at one end thereof to a first pivotal attachment point on the support base and slidably attached at a second end thereof to the C-arm, wherein the first pivotal attachment point coincides with an axis of lateral rotation such that the support arm is selectively rotatable relative to the support base about said axis of lateral rotation to selected lateral positions;
  a gas spring pivotally attached to a second pivotal attachment point on the support base and extending away from said second pivotal attachment point into a third attachment point on the support arm, wherein said second pivotal attachment point is spaced apart from the first pivotal attachment point;
  wherein the support arm, C-arm, X-ray source and image receptor collectively comprise an X-ray assembly having a center of mass, and wherein the second pivotal attachment point resides below the first pivotal attachment point to thereby enable the gas spring to apply a counteracting torsional force against an out-of-balance torsional force produced when the center of mass of the X-ray assembly resides out of vertical alignment with the axis of lateral rotation;
  wherein a majority portion of the support arm comprises an elongate member and wherein the gas spring comprises an elongate member, and wherein said gas spring is disposed in a nonparallel orientation with respect to said majority portion of the support arm for a majority of positions of said support arm relative to the support base to thereby produce a desired amount of torsional force about the axis of lateral rotation;
  wherein the C-arm and the X-ray source and the image receptor and the support arm collectively comprise an X-ray assembly having a center of mass that resides below the axis of lateral rotation when the support arm resides in a first, unrotated position;
  wherein the center of mass of the X-ray assembly resides at least three inches below the axis of lateral rotation when the support arm resides in the first, unrotated position;
  wherein a line extending between the second pivotal attachment point and the third attachment point is nonhorizontal and nonvertical for a for a majority of positions of the support arm relative to the support base when the X-ray positioning apparatus is disposed in a normal, operative working position, such that rotational movement of the support arm about the axis of lateral rotation produces pivotal movement at the third attachment point in multiple planes, and wherein the third attachment point comprises a universal joint;
  wherein the second pivotal attachment point resides below the first pivotal attachment point and above a center of mass of the X-ray system when the support arm resides in a first, unrotated position;
  wherein the second pivotal attachment point resides below the first pivotal attachment point by a distance within a range of approximately one inch to two inches, and wherein the center of mass of the X-ray system resides below the axis of lateral rotation by a distance of at least three inches;
  wherein the gas spring includes a means for applying a compression force to the support arm, said gas spring being connected to the support arm and to the support base in an arrangement which, in combination with the compression force, operates to produce a counteracting torsional force about the axis of lateral rotation substantially equivalent to an opposing torsional force produced about said axis of lateral rotation by force of gravity when the support arm is disposed in a displaced, rotated position;
  wherein the C-arm and the X-ray source and the image receptor and the support collectively comprise an X-ray assembly having a center of mass, and wherein said center of mass being spaced-apart from the axis of lateral rotation by a separation distance and is thereby disposed in an orbital movement path about said axis of lateral rotation by rotational movement of the support arm, and wherein a combination of the separation distance and amount of weight of the X-ray assembly requires the compression force applied by the gas spring to exceed nine hundred pounds in order to produce the counteracting torsional force that is substantially equivalent to the opposing torsional force produced by force of gravity;
  wherein the support arm comprises an elongate member having a central axis, and wherein the gas spring comprises an elongate member having a central axis that remains in a nonparallel orientation with respect to the central axis of the support arm;
  wherein the entire gas spring resides inside the support arm;
  wherein the gas spring comprises an expansion/contraction means for expanding responsive to upward pivotal movement of at least a portion of the suspension means and contracting responsive to downward pivotal movement of said portion of the suspension means.

46. The apparatus of claim 36, wherein the reinforcing means is pivotally coupled to the support base at a fixed point.

* * * * *